United States Patent [19]

Elloy

[11] Patent Number: 5,169,402
[45] Date of Patent: Dec. 8, 1992

[54] SURGICAL INSTRUMENT

[75] Inventor: Martin A. Elloy, Church Fenton, Great Britain

[73] Assignee: Chas. F. Thackray Ltd., Leeds, United Kingdom

[21] Appl. No.: 678,981

[22] PCT Filed: Oct. 9, 1989

[86] PCT No.: PCT/GB89/01188
§ 371 Date: Apr. 29, 1991
§ 102(e) Date: Apr. 29, 1991

[87] PCT Pub. No.: WO90/03764
PCT Pub. Date: Apr. 19, 1990

[30] Foreign Application Priority Data

Oct. 8, 1988 [GB] United Kingdom ............. 8823669

[51] Int. Cl.⁵ .............................................. A61B 17/56
[52] U.S. Cl. ................................... 606/85; 606/79
[58] Field of Search ............................. 606/79-84, 606/85

[56] References Cited

U.S. PATENT DOCUMENTS 4,466,429  8/1984  Loscher et al. ............. 606/85 X
4,777,942  10/1988 Frey et al. .................. 606/85 X Primary Examiner—Robert A. Hafer
Assistant Examiner—Kevin G. Rooney
Attorney, Agent, or Firm—Merchant, Gould, Smith, Edell, Welter, & Schmidt

[57] ABSTRACT

There is disclosed a surgical instrument for use in preparing a bone cavity for the subsequent implantation of a joint replacement prosthesis, and especially for the enlargement of a medullary cavity of a femur prior to the implantation of a femoral component of a hip prosthesis. The instrument comprises a shank (2) having serrations (4) on at least a part of its outer surface and a handle (3) mounted at one end of the shank, in which the shank is divided into a main body member (5) and at least one sliding member (6) which is engageable with the main body member in such a way as to allow relative sliding motion between the sliding member and the main body member during use of the instrument, so that the serrations can shape the interior surface of the bone cavity.

12 Claims, 6 Drawing Sheets

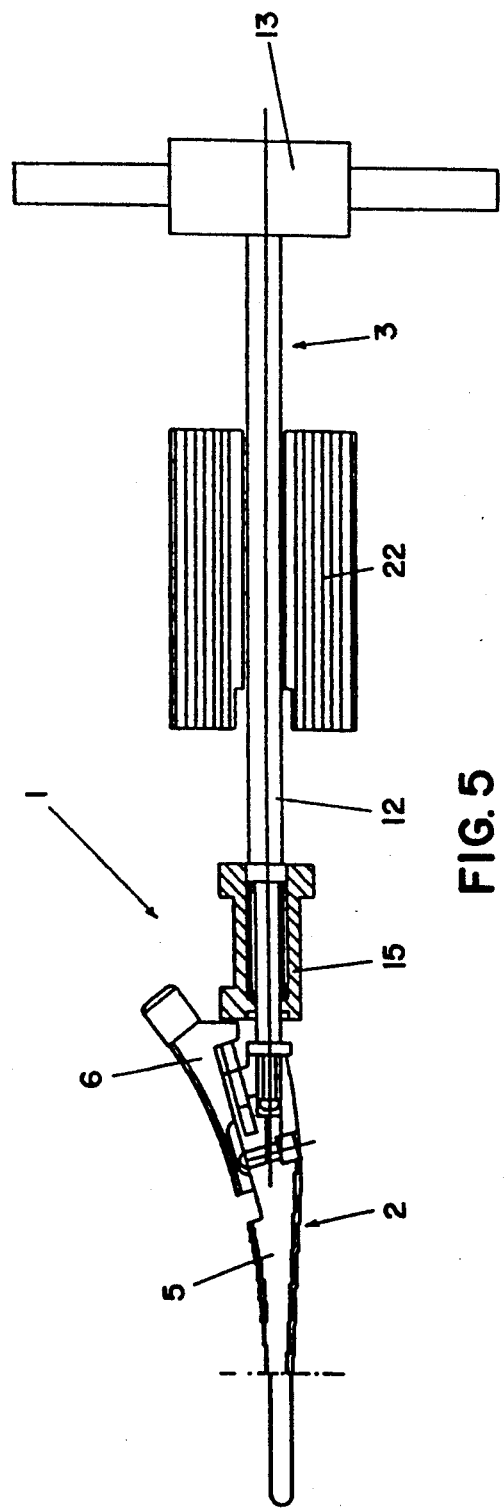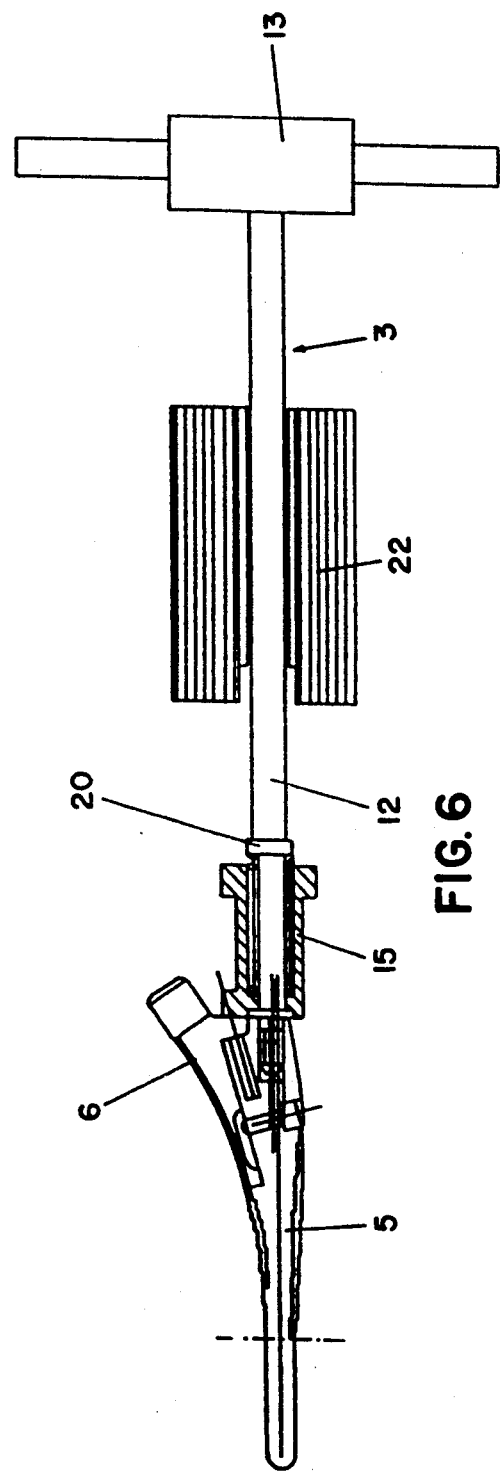

SURGICAL INSTRUMENT

This invention relates to a surgical instrument for use in preparing a bone cavity for the subsequent implantation of a joint replacement prosthesis.

The invention has been developed primarily, though not exclusively, in relation to a surgical instrument for enlarging and shaping the natural medulla of a femur for the subsequent implantation of the femoral component of a hip prosthesis.

Conventionally, this is done by using a broach or rasp which comprises a handle and a serrated shank joined to the handle, the serrated shank being shaped to correspond to the shape of the stem of the femoral component to be implanted.

The disadvantage of such a conventional rasp is that, for accuracy, the rasp must be moved in a straight line, preferably parallel to the shaft of the femur. However, such a direction of movement does not produce a proper cutting action on the bone surfaces which are far from parallel to the direction of movement of the rasp, particularly the medial cortex, but also anterior and lateral cortices, and sometimes the posterior cortex.

According to the invention there is provided a surgical instrument for use in the shaping of a bone cavity prior to the implantation of a joint replacement prosthesis, in which the instrument comprises a shank having serrations on at least a part of its outer surface and a handle mounted at one end of said shank, said shank being divided into a main body member and a slidable member which is engageable with said main body member in such a manner as to allow relative sliding motion between the slidable member and the main body member during use of the instrument, in order that the serrations can carry out the required shaping of the bone cavity.

A surgical instrument according to the invention is applicable generally to the shaping of a bone cavity in preparation for the subsequent implantation of a replacement joint prosthesis, but is particularly suitable for use in preparing i.e. enlarging the medullary cavity of a femur prior to implantation of a femoral component of a hip prosthesis.

Preferably, the sliding movement between the main body member and the slidable member of the shank is limited at each of its two extreme positions by a pair of stops located on the slidable member and engageable by a protrusion carried on the body member. Alternatively, the stops are provided on the body member and are engageable by a protrusion carried on the slidable member.

Conveniently, a single slidable member is provided, which is arranged relative to the main body member such that its outer, bone cutting surface prepares the medial surface of the cavity in the femur. However, additional slidable members may be provided, arranged appropriately to prepare the anterior, posterior and lateral surfaces of the cavity.

The sliding member is preferably located at the end of the shank closest to the handle, such that as the instrument is inserted into the femoral medulla the outer surface of the sliding member will engage the calcar and will be retained whilst the main body member is caused to penetrate deeper within the medulla, with the result that the sliding member slides along the main body member towards the handle.

By applying force to the exposed end of the sliding member, the latter can be forced into the femoral medulla, and these two actions are repeated alternately until the whole shank of the instrument has been fully inserted in the femoral medulla. This ensures that the medulla is enlarged to exactly the right size and shape to fit the stem of the femoral component, without cutting too much bone away in the process of preparing the femur. Preferably, the main body member and the sliding member each include guide means which cooperate to restrict said relative sliding movement to a single plane. However, the sliding movement may alternatively be along an arc. In either case, the choice of slide angle, either plane or arc, should be such that it avoids overcutting of the bone during operation. A good compromise is to restrict the sliding movement to a plane tangential to the medial curvature of the sliding member at its most distal end.

The handle is preferably releasably connected to the shank, or alternatively it may be fixedly mounted on the shank.

In the preferred embodiment the handle comprises an elongate rod having a first end for connection to said shank and a second end having a gripping device mounted thereon.

There is conveniently provided adjacent said first end a housing which is mounted around said rod and is slidable therealong, the housing having a first end which is engageable with an exposed end of the slidable member, and a second end spaced from said first end along the longitudinal axis of the rod. A spring is provided around the rod between the rod and the housing, one end of which bears against the internal wall of the housing and the other end of which bears against a stop on the rod.

Thus, as the instrument is pushed into the medulla by applying force to the handle, the sliding member of the shank slides along the main body member and its exposed end abuts the first end of the housing on the rod of the handle. This compresses the spring and causes the housing to slide along the rod towards the gripping device. When the surgeon observes that this has happened, he then operates a slide hammer which is slidably mounted around the rod of the handle, and hammers on the second end of the housing until it assumes its former position.

Clearly, the resilience of the spring determines the frictional force necessary on the sliding member to cause it to slide along the main body member.

Embodiments of the present invention will now be described by way of example only with reference to the accompanying drawings, in which.

Figure 1:
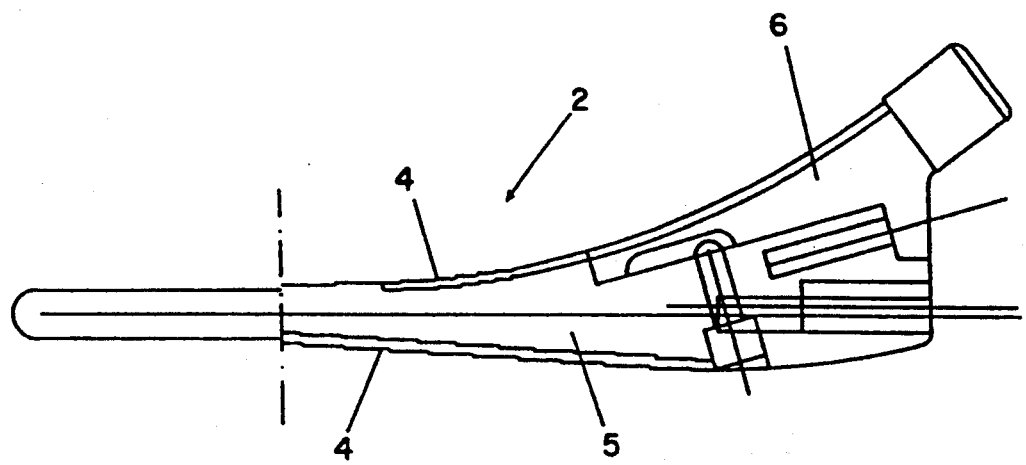
FIG. 1 is a side view of part of a first embodiment of instrument in accordance with the present invention having a shank provided with a main body member, and a single slidable member co-operating therewith.
Figure 2:
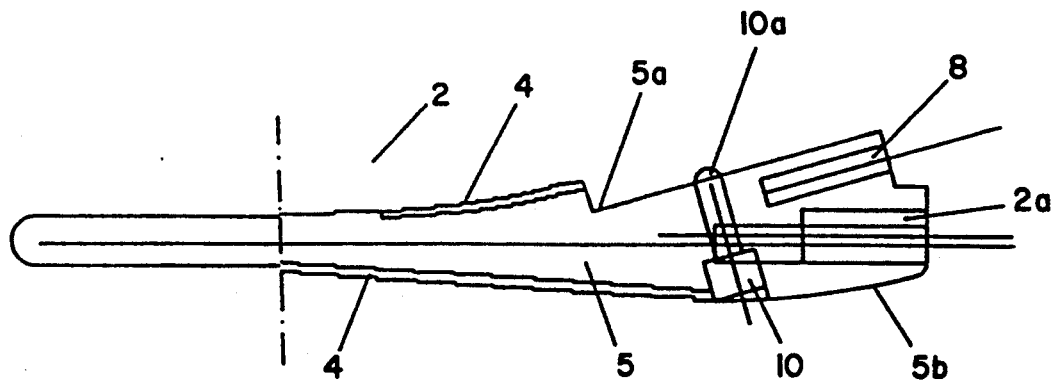
FIG. 2 is a side view of the main body member of the shank of the instrument of FIG. 1.
Figure 3:
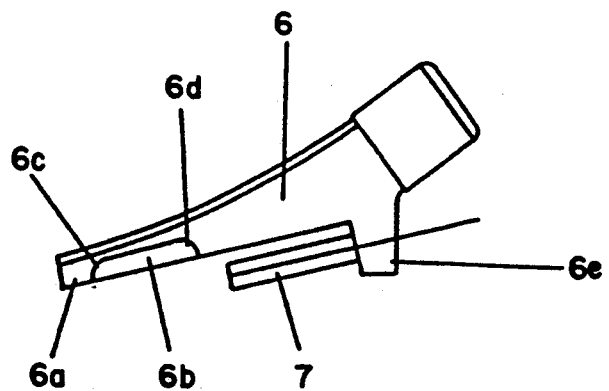
FIG. 3 is a side view of the sliding member of the shank of the instrument of FIG. 1.
Figure 4:
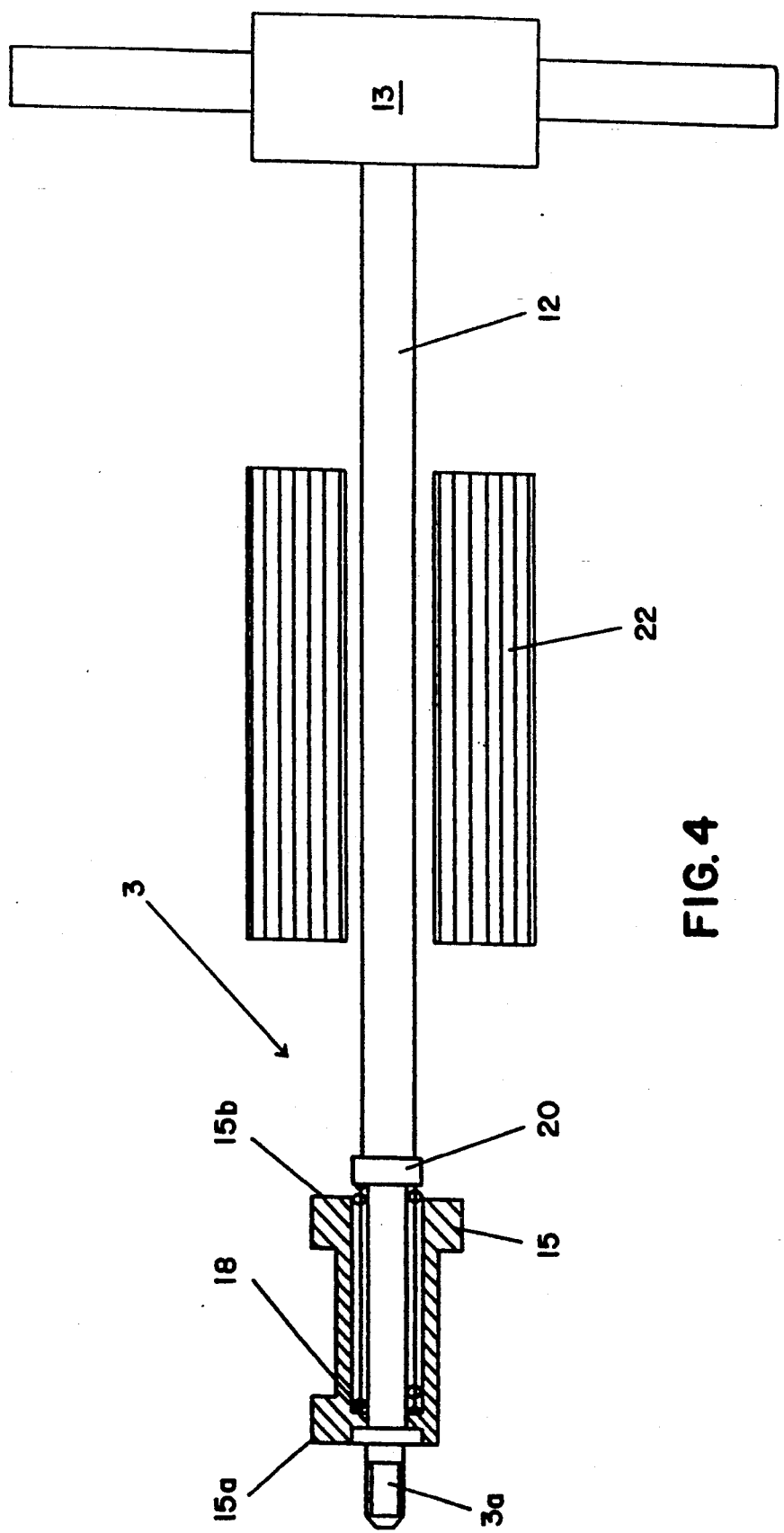
FIG. 4 is a side view of the handle forming part of the instrument.
Figure 7:
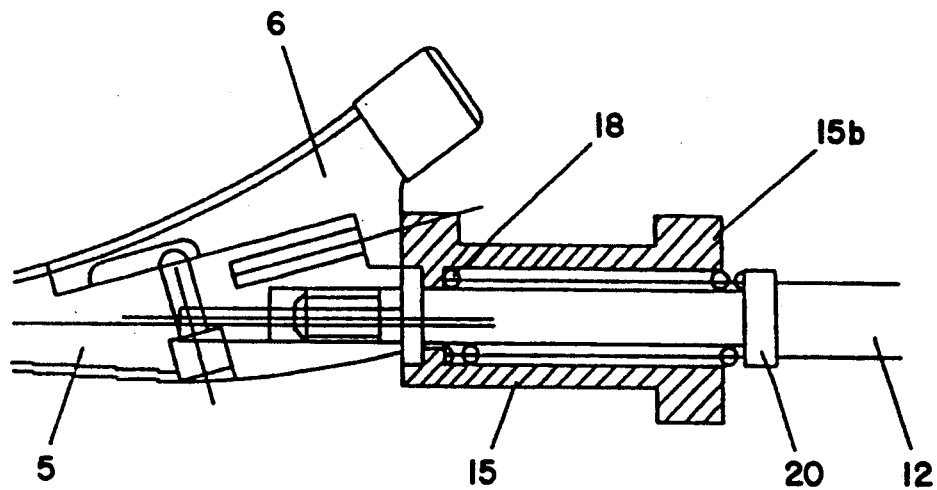
Figure 8:
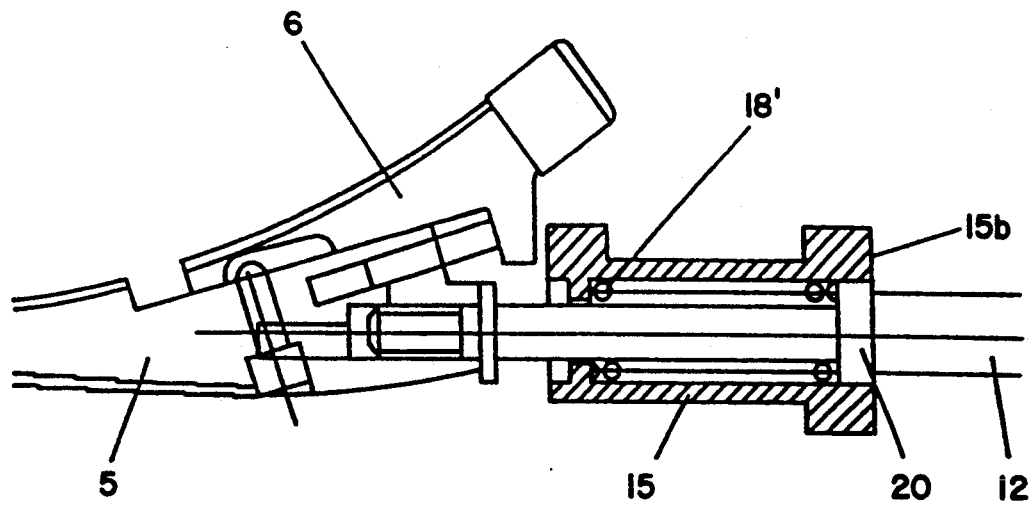
Figure 10:
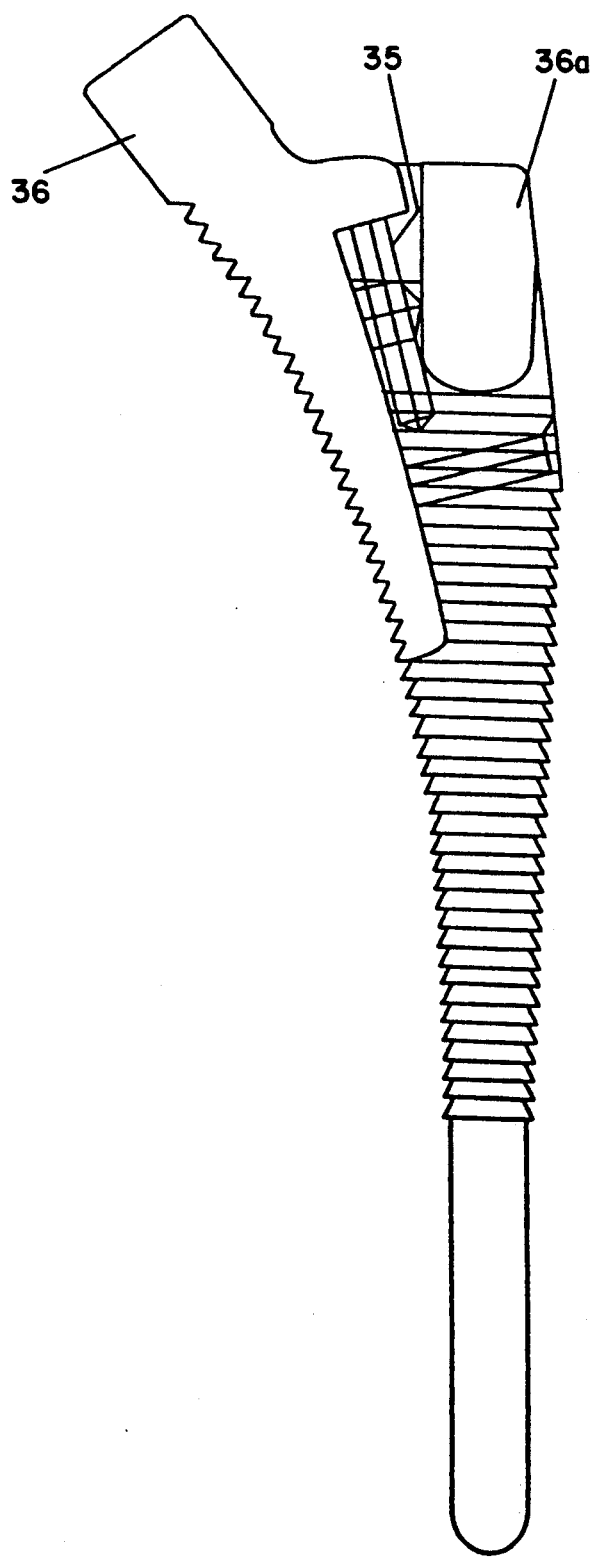
Figure 11:
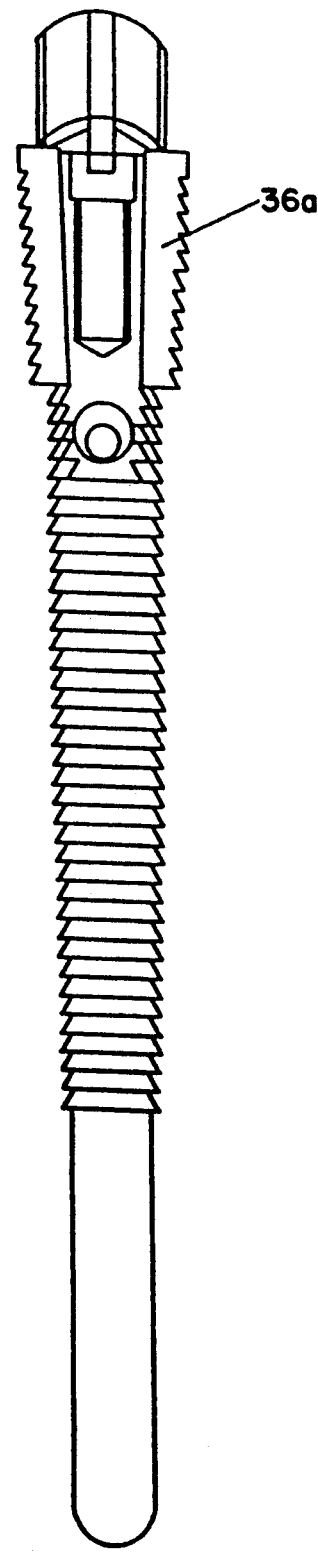
Figure 9:
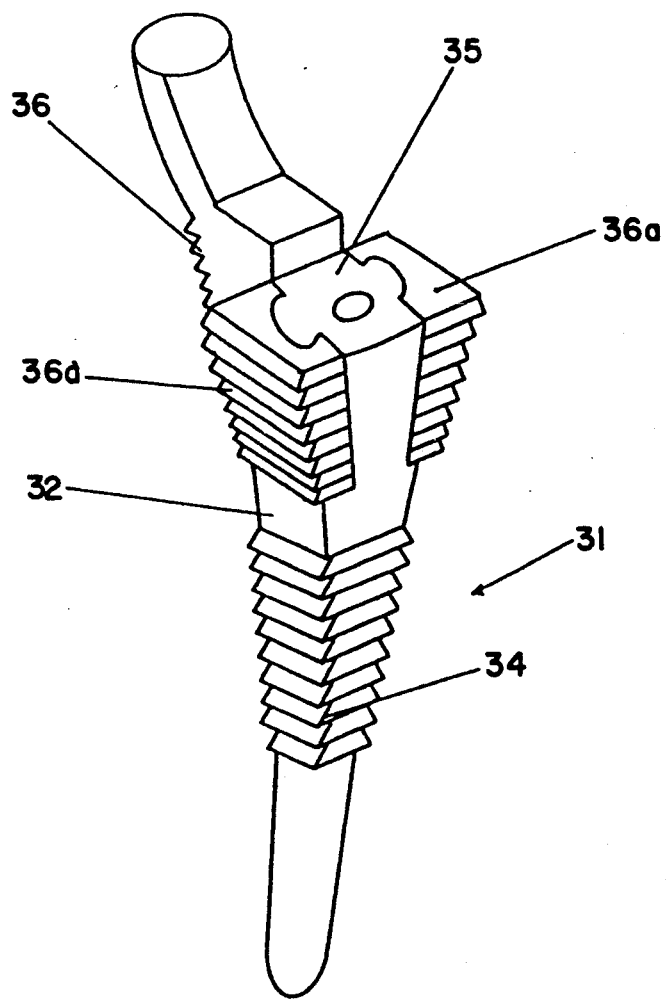
Figure 12:
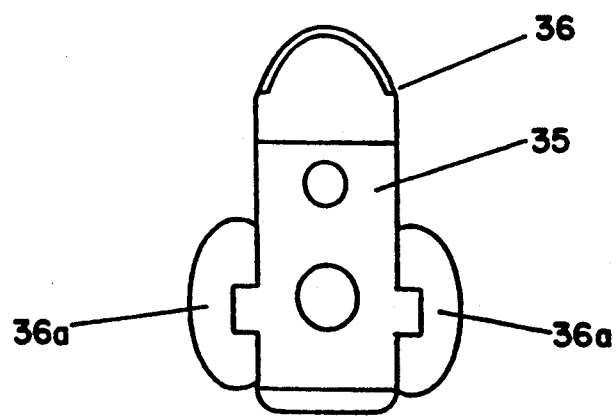

FIGS. 5 and 6 illustrate the use of the handle to insert the instrument in the femoral medulla; and FIGS. 7 and 8 show parts of FIGS. 5 and 6 enlarged;

FIG. 9 is a perspective view of a further embodiment of instrument in accordance with the invention and having a plurality of slidable members;

FIG. 10 is a side view, to an enlarged scale of the instrument shown in FIG. 9;

FIG. 11 is a plan view, corresponding to FIG. 10; and,

FIG. 12 is an end view, corresponding to FIGS. 10 and 11.

Referring to FIGS. 1 to 8 of the drawings, a surgical instrument or rasp 1 for use in the enlargement of the medullary cavity of a femur prior to implantation of a femoral component of a hip prosthesis comprises a shank 2 and a handle 3 releasably connected to the shank by means of a threaded end 3a which engages the threaded hole 2a in the shank 2.

The shank portion has a number of serrations 4 on its outer, bone cutting surface which serve to ream out the medullary cavity when the shank is inserted therein.

The shank 2 comprises a main body member 5 and a separate sliding member 6 which is engagable with the main body member 5 such as to allow relative sliding motion between the portions 5 and 6 over the mating surfaces 5a, 6a. In the illustrated embodiment, the sliding member 6 is arranged so as to prepare the medial surface of the femoral cavity.

A guide rod 7 on the sliding member 6 locates within a corresponding hole 8 in the main body member such as to limit the sliding movement to a single plane.

A cavity 6b in the surface 6a is bounded by stops 6c, 6d, these stops being engaged by the protruding end 10a of a pin 10 in the main body member 5, such that the relative sliding movement of the two members 5 and 6 is limited at the two extreme positions shown in FIGS. 5 and 6.

The handle 3 comprises an elongate rod 12 having a gripping device 13 fixed at one end thereof. At the other end of the rod 12, adjacent the threaded end 3a, there is a housing 15 which surrounds the rod 12 and is slidable there along. One end 15a of the housing 15 abuts against the end face 6e of the sliding member 6, and inside the housing there is a spring 18 which is located around the rod, between the rod 12 and the housing 15. One end of spring 18 bears against the inside of the housing 15, and the other end of spring 18 bears against a stop 20 on rod 12.

A slide hammer 22 is slidably mounted around rod 12 and is operable to hammer against end 15b of housing 15, which in turn applies a hammering force to end face 6e of sliding member 6.

To use the instrument, the surgeon first of all uses the grip 13 to push the shank 2 into the femoral medulla. However, as soon as the sliding member 6 engages the calcar it will be arrested as the main portion 5 is pushed deeper into the medulla, causing the sliding member 6 to slide along main portion 5 towards the handle 3 which in turn pushes housing 15 along rod 12 towards the gripping device 13, thus compressing spring 18. When the end 15b of housing 15 is approximately level with stop 20, as in FIGS. 5 and 7, the surgeon operates the slide hammer 22 against end 15b of housing 15, thus hammering the sliding member 6 via housing 15 more fully into the femoral medulla. He continues with this hammering operation until the stop 20 again protrudes from the housing 15 as in FIGS. 6 and 8. The surgeon repeats these two stages alternately until the whole of the shank portion 2 is fully inserted within the femoral medulla.

The chamfer 5b on the lateral side of the rasp is designed to clear the overhand of the trochanter and allow proper alignment before the rasp makes its final sizing cuts.

The embodiment described above and illustrated in FIGS. 1 to 8 has a single sliding member 6. However, a surgical instrument in accordance with the invention may be provided with a plurality of sliding members, and further embodiments of the invention are therefore shown, and will be described in more detail below with reference to FIGS. 9 to 12.

FIG. 9 is a perspective and schematic illustration of a surgical instrument according to the invention which is designated generally by reference 31, and which comprises a shank 32 provided with serrations 34 for carrying out any required shaping of the interior of a bone cavity, such as the medula of a femur, and has a main body portion 35.

A slidable member 36 is mounted on the shank 32 for slidable movement relative to the main body number 35 in generally similar manner to the mounting of the sliding member 6 relative to the main body member 5 in the first embodiment. However, in addition there are two lateral sliding members 36a arranged one along each side of the main body member 35, and also capable of forward and rearward sliding movement relative to the main body member 35.

FIG. 9 is a perspective illustration of this multiple sliding member embodiment, and FIGS. 10 to 12 show this embodiment to an enlarged scale, and in which corresponding parts are designated by the same reference numerals. The three sliding members will be movable forwardly by forward impact of the hammer 22, which is able to engage suitably projecting exposed faces of the sliding members.

The illustrated embodiments of surgical instrument according to the invention are particularly suitable for use in shaping the natural medula of a femur for the subsequent implantation of the femoral component of a hip prosthesis, but of course it should be understood that the instrument can have general application in the surgical implantation of replacement joint prostheses, by shaping of the appropriate bone cavities.

I claim:

1. A surgical instrument for use in the shaping of a bone cavity prior to the implantation of a joint replacement prosthesis, in which the instrument comprises a shank having an outer surface of predetermined shape and serrations on at least a part of the outer surface, and a handle mounted at one end of said shank, said shank being divided into a main body member on which the handle is mounted and a slidable member having an outer bone cutting surface which forms part of the outer surface of the shank, which slidable member is engageable with said main body member in such a manner as to allow relative sliding motion between slidable member and the main body member during use of the instrument, in order that the serrations can carry out the required shaping of the bone cavity, the shape of the bone cavity being determined by the predetermined shape of the outer surface of the shank.

2. A surgical instrument according to claim 1, in which the sliding movement between the main body member and the slidable member is limited at each of two extreme positions by a pair of stops located on the slidable member and engageable by a protrusion carried on the body member.

3. A surgical instrument according to claim 1, in which the sliding movement between the main body member and the slidable member is limited at each of its two extreme positions by stops provided on the body member engageable by a protrusion carried on the slidable member.

4. A surgical instrument according to claims 1, in which a single slidable member is provided, which is arranged relative to the main body member such that its outer bone cutting surface can prepare the medical surface of the cavity in a femur, when the instrument is used in the enlargement of the natural medulla of a femur.

5. A surgical instrument according to claim 4 in which additional slidable members are engaged with said body member to prepare the anterior, posterior and lateral surfaces of the cavity.

6. A surgical instrument according to claim 1, in which the slidable member is located at the end of the shank closest to the handle, so that is the instrument is inserted into a femoral medulla, the outer surface of the slidable member can engage the calcar and be retained whilst the main body member is caused to penetrate deeper within the medulla, with the result that the slidable member slides along the main body member towards the handle.

7. A surgical instrument according to claim 1, in which the main body member and the slidable member each include guide means co-operable to restrict the relative sliding movement to a single plane.

8. A surgical instrument according to claim 1, in which the main body member and the sliding member each include guide means which co-operate to restrict the relative sliding movement to movement along an arc.

9. A surgical instrument according to claim 1, in which the handle is releasably connected to the shank.

10. A surgical instrument according to claim 1, in which the handle comprises an elongate rod having a first end for connecting said shank and a second end having a gripping device mounted thereon.

11. A surgical instrument according to claim 10, in which a housing is mounted adjacent to said first end of said rod and is slidable there along, the housing having a first end which is engageable with an exposed end of the slidable member, and a second end spaced from said first end along the longitudinal axis of the rod, and a spring being provided around the rod between the rod and the housing, one end of which bears against the internal wall of the housing and the other end of which bears against a stop on the rod.

12. A surgical instrument according to claim 11, in which a hammer is slidably mounted on the handle for movement toward and away from impact with said second end of the housing.

* * * * *